United States Patent
Brooks et al.

(10) Patent No.: US 10,713,920 B2
(45) Date of Patent: *Jul. 14, 2020

(54) WEARABLE COMPUTING DEVICE FOR MONITORING HAZARDS

(71) Applicant: VORBECK MATERIALS CORP., Jessup, MD (US)

(72) Inventors: Louise Brooks, Washington, DC (US); Sriram Manivannan, Baltimore, MD (US); Paige Boehmcke, Baltimore, MD (US); Matthew Guenette, Baltimore, MD (US); James Brent, Glenwood, MD (US)

(73) Assignee: VORBECK MATERIALS, CORP., Jessup, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/202,029

(22) Filed: Nov. 27, 2018

(65) Prior Publication Data

US 2019/0096225 A1  Mar. 28, 2019

Related U.S. Application Data

(63) Continuation of application No. 15/479,030, filed on Apr. 4, 2017, now Pat. No. 10,169,978.

(Continued)

(51) Int. Cl.
*G08B 21/00* (2006.01)
*G08B 21/18* (2006.01)
(Continued)

(52) U.S. Cl.
CPC .......... *G08B 21/182* (2013.01); *A41D 1/005* (2013.01); *A61B 5/0205* (2013.01); *A61B 5/6805* (2013.01); *G06F 1/163* (2013.01); *G06F 1/1698* (2013.01); *G06F 11/3051* (2013.01); *G06F 11/3055* (2013.01); *G06F 11/3058* (2013.01); *G06F 11/3089* (2013.01); *G08B 21/02* (2013.01); *A41D 2600/20* (2013.01); *A61B 5/0008* (2013.01); *A61B 5/0022* (2013.01); *A61B 5/02438* (2013.01);
(Continued)

(58) Field of Classification Search
CPC ...... G08B 13/08; G08B 21/02; G08B 21/182; A41D 1/005
USPC ..................................................... 340/691.8
See application file for complete search history.

(56) References Cited

U.S. PATENT DOCUMENTS

| | | | | |
|---|---|---|---|---|
| 6,606,993 | B1 * | 8/2003 | Wiesmann | A62B 9/006 128/204.23 |
| 2013/0157713 | A1 * | 6/2013 | Stolarczyk | H04M 1/026 455/550.1 |

(Continued)

*Primary Examiner* — Mark S Rushing
(74) *Attorney, Agent, or Firm* — Trentice V. Bolar, Esq.

(57) ABSTRACT

Embodiments of the present invention relate to wearable computing devices. In some embodiments, a wearable computing devices ("WCD") for monitoring occupational hazards are disclosed. The WCD may include an apparel item having one or more control circuits affixed thereto. One or more sensors may be communicatively coupled to the computing device and configured to detect or monitor at least one of an aspect of a user of the WCD and an ambient environment of the user. The control circuits can be configured to generate one or more notifications when sensor data comprises a value above a threshold amount.

15 Claims, 2 Drawing Sheets

Related U.S. Application Data

(60) Provisional application No. 62/317,912, filed on Apr. 4, 2016.

(51) Int. Cl.
| | |
|---|---|
| *A41D 1/00* | (2018.01) |
| *A61B 5/00* | (2006.01) |
| *G06F 11/30* | (2006.01) |
| *A61B 5/0205* | (2006.01) |
| *G06F 1/16* | (2006.01) |
| *G08B 21/02* | (2006.01) |
| *A61B 5/024* | (2006.01) |

(52) U.S. Cl.
CPC ... *A61B 2503/20* (2013.01); *A61B 2560/0242* (2013.01); *A61B 2562/0219* (2013.01); *A61B 2562/12* (2013.01)

(56) References Cited

U.S. PATENT DOCUMENTS

2015/0173674 A1* 6/2015 Hayes .................... A61B 5/681
 600/301
2017/0184528 A1* 6/2017 Haque ................ H01L 51/0045

\* cited by examiner

FRONT

WEARABLE COMPUTING DEVICE FOR MONITORING HAZARDS

CROSS-REFERENCE TO RELATED APPLICATIONS

The present application is a continuation of U.S. patent application Ser. No. 15/479,030, filed Apr. 4, 2017, which claims priority to U.S. Provisional Application No. 62/317,912 filed Apr. 4, 2016, and is hereby incorporated by reference in its entirety.

TECHNICAL FIELD

Background

The present invention relates generally to wearable computing devices and specifically to wearable computing devices for the communication and monitoring of environmental conditions and biometric data. Remote workers that operate in hazardous environments may dispatched thereto with one or more partners to reduce the occurrence of accidents. In such situations, employers are required employ a plurality of workers where such work may require the use of one or less workers. Hazardous work environments may further require businesses to acquire expensive insurance plans, which further increase expenditures. In addition, such environments typically require employers to provide remote workers an above average compensation package.

DETAILED DESCRIPTION

As used herein "remote employees" refers to employees that work alone or in an unsupervised environment. For example, industries that involve oil and gas exploration and refinement, logging/timber, as well as transportation typically involve a plurality of remote employees. However, remote employees can face fatality rates that are higher than the general industrial rate.

Figure 1A:
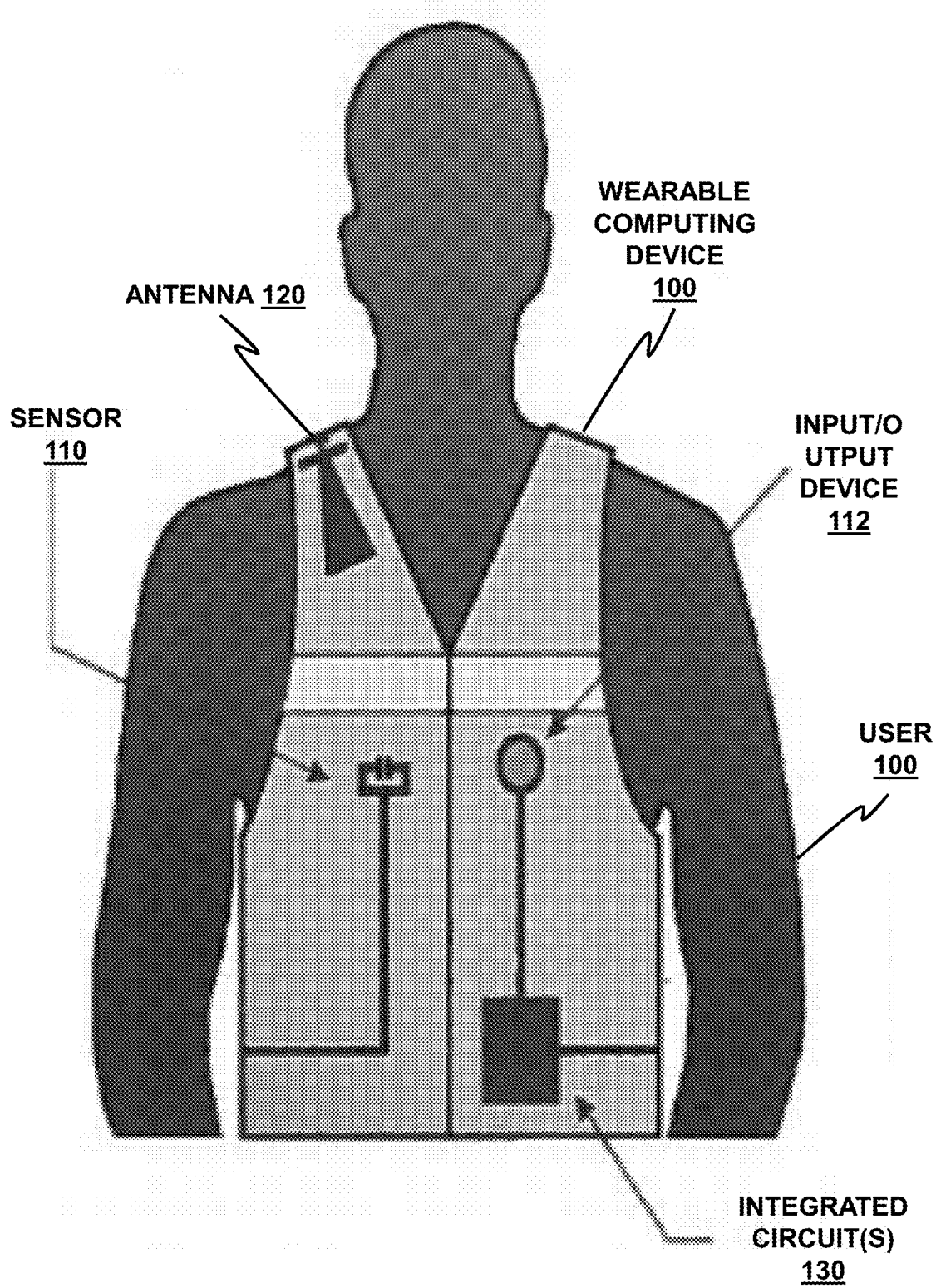
FIG. 1A depicts a front view of a wearable computing device, in accordance with some embodiments.
Figure 1B:
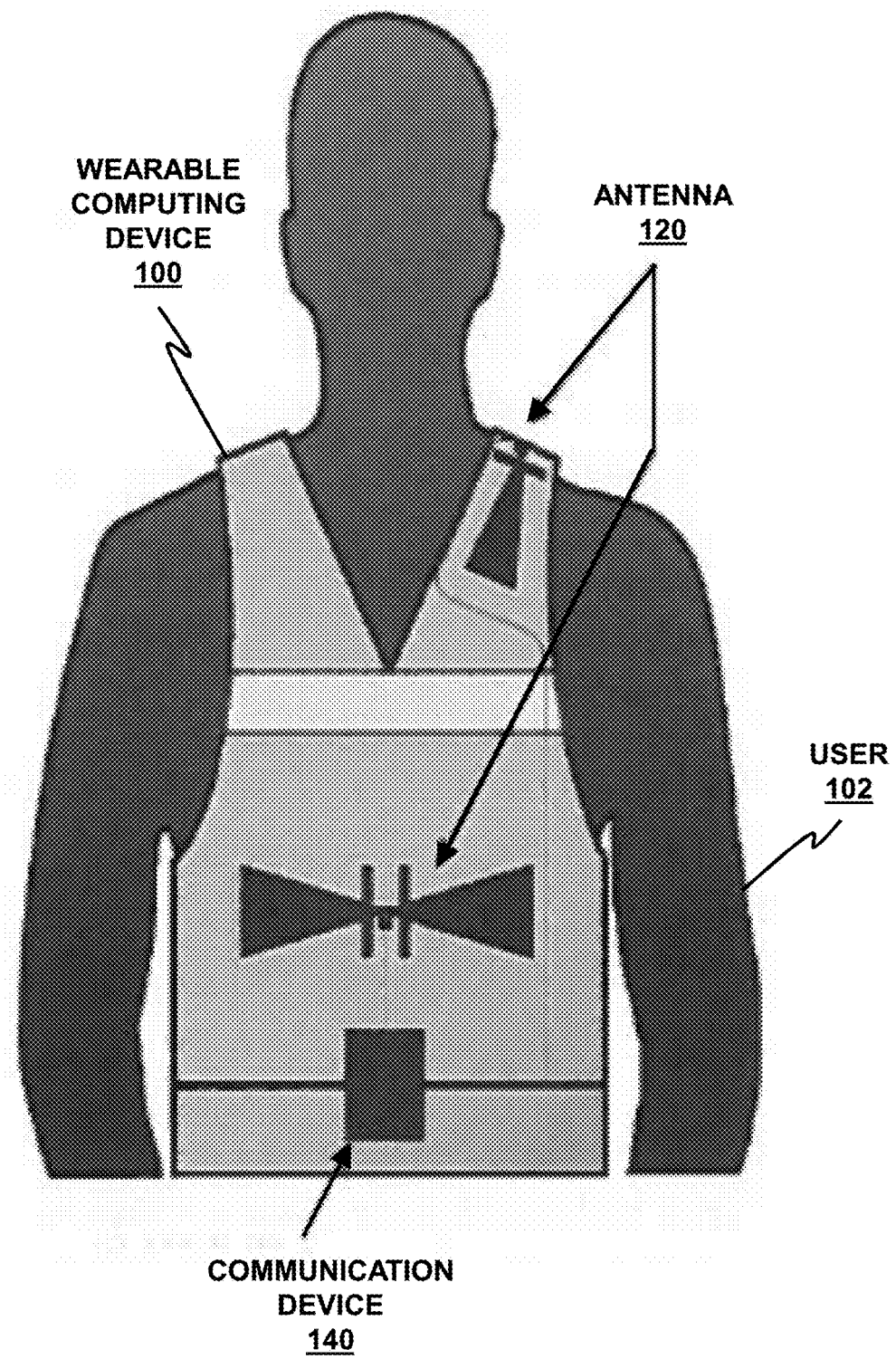
FIG. 1B depicts a back view of a wearable computing device, in accordance with some embodiments.

Referring now to FIGS. 1A and 1B. In some embodiments, a wearable computing device ("WCD") 100 for monitoring remote workers can include an apparel item having one or more integrated circuits ("IC") 130 affixed thereto, one or more input/output devices 112 communicatively coupled to the ICs 130, and one or more sensors 110 communicatively coupled to one or more of the integrated circuits 130. In some embodiments, the one or more ICs 130 can be configured to execute at least a portion of the steps, processes, methods disclosed in one or more of the embodiments disclose herein. The WCDs 100 can be configured to facilitate the monitoring of and/or communication with remote workers to facilitate the mitigation of one or more occupational hazard risks associated with remote workers.

In some embodiments, the WCD 100 may also include one or more information storage devices communicatively coupled to the integrated circuits 130. In some embodiments, each of the one or more storage devices can store at least a portion of the data generated by the sensors 110. In some embodiments, the WCD 100 can include one or more communication device 140 communicatively coupled to the one or more integrated circuits 130 that can allow one-way or two-way communication. For example, communication device 140 can be configured to communicate other WCDs 100, cellular towers, a central control unit, or a combination of two or more thereof. In some embodiments, the communication device 140 can each be communicatively coupled to one or more antennas 120. For example, each of the one or more antennas 120 can be secured to the shoulder region, torso region, front-facing region, back-facing region, or a combination of two or more regions of the WCD 110.

In some embodiments, the sensors 110 can include one or more (i) CO and/or $CO_2$ pressure sensors; (ii) oxidizing gas pressure sensors; (iii) temperature sensors; (iv) humidity sensors; (v) EMF sensors; (vi) biometric sensors; (vii) barometers; (viii) altimeters; (ix) haptic sensors; (x) geospatial sensors; (xi) proximity sensors; and/or (xii) accelerometers. In some embodiments, the sensors 110 can be configured to detect and/or measure one or more chemical agents that may have a harmful effect on biological systems (e.g., humans and/or other mammals). For example, the sensors 110 can be configured to detect and/or measure liquid propane gas, methane (i.e., natural gas), carbon monoxide, petrochemicals, similar chemicals that may exhibit harmful effects to biological systems (e.g., humans and/or other mammals), or a combination of two or more thereof.

In some embodiments, the sensors 110 can be configured to detect and/or measure one or more biological and physical agents that may have a harmful effect on biological systems (e.g., humans and/or other mammals). In some embodiments, the sensors 110 can include one or more components that include graphene-based conductive compositions. In some embodiments, the sensors 110 can be configured to detect and/or measure biometric events (e.g., respiratory rate, heartrate, or a combination of the two). In some embodiments, the I/O devices 112 can also be configured to emit an output (e.g., audible, haptic, visual, similar output, or a combination of two or more thereof) in response to the measured and/or detected input of the sensors 110 (e.g., when such data is above a first threshold amount or below a second threshold amount).

For example, one or more outputs can be emitted by the I/O devices 112 when one or more chemical, biological, physical, similar agents that may be harmful to biological systems are determined to be above a threshold amount. By one approach, one or more outputs can be emitted by the I/O devices 112 when one or more chemical and/or life supporting chemicals (e.g., oxygen) are is determined to be below a threshold amount. In some embodiments, the outputs emitted by the I/O devices 112 can alert user 102 to the presence of potential threats in the ambient environment and thereby may increase the safety of the user 102. In some embodiments, one or more of the sensors 110 can be configured to capture geolocation data corresponding to the position/location of user 102.

Captured geolocation data (e.g., data associated with GPS, time difference of arrival, Wi-Fi positioning, latitude/longitude, similar coordinate data, or a combination of two or more thereof) can be transmitted (e.g., via the communication devices 140) to other users 102 and/or observers of users 102 (i.e. supervisors). In some embodiments, information captured by the sensors 110 may be used to notify other users 102 and/or observers of users 102 when a particular user 102 enters a hazardous environment and/or engages in hazardous behavior (e.g., behavior that falls outside of the rule/regulations defined by the Occupational Safety and Health Act ("OSHA"), an employer of the user 102, an associated industry standard, similar behavior, or a combination of two or more thereof).

Information captured by one or more of the sensors 110 can be transmitted (e.g., via communication devices 140) to other users 102 and/or observers of users 102 (i.e. supervisors). For example, WCDs 100 can include one or more communication devices 140 that can be configured to transmit and/or receive data (e.g., voice, text, and/or graphical). The WCDs 100 can comprise one or more input/output devices 112 communicatively coupled to the ICs 130. In some embodiments, input/output devices 112 can a microphone and/or a speaker in electrical communication with the communications unit. In some embodiments, communication devices 140 can be configured to operate using one or more wireless communications standards, including but not limited to Long Term Evolution ("LTE"), 4G, 5G, as well as similar cellular communications standards. Communications device 140 can increase the number of remote workers observers can track, monitor, detect, observe, supervise, oversee, advise, inspect, examine, scrutinize, similar activities, or a combination of two or more thereof. Each WCD 100 can include one or more antennas 120 positioned thereto and communicatively coupled to the one or more communications devices 140.

In some embodiments, antennas 120, sensors 110, input/output devices 112, circuits, and/or conductive traces can include one or more components that include a conductive composition ("the composition"). The composition can comprise graphene sheets. In some embodiments, the graphenic material can include individual sheets of graphene. By one approach, the individual sheets of graphene can form a three-dimensional network (e.g., a percolated network) within the composition. The composition can be applied directly on to WCD 100. The composition can be applied on to one or more surfaces of a substrate of which may be subsequently applied on to the WCD 100. In some embodiments, the composition can be applied via a plurality of printing techniques, including but not limited to, screen, flexographic, gravure, and offset. By one approach, the compositions can be configured to form flexible components, antennas, sensors, I/O devices, circuits, and/or conductive traces.

Workers can operate in a plurality of biomes (e.g., tundra, taiga, deciduous forest, grasslands, desert, high plateaus, tropical forest, minor terrestrial biomes, marine, terrestrial, and/or similar bio), environments (e.g., hot, cold, dry, wet, etc.), and ecosystems that each require workers to wear a particular type of apparel items to execute their work with a degree of comfort and/or protect themselves from one or more environmental factors (e.g., heat, cold, moisture, biological factors. For example, the WCDs 100 can be any type of apparel item, including but not limited to, a vest, form fitting apparel items, undergarments (e.g., apparel items configured to be worn on the torso or lower extremities under other garments), outerwear (e.g., coat, cloak, jacket, hoodie, smock, apron, poncho, and other), and harnesses.

In some embodiments, the WCD 100 can comprise one or more data stores in communication with the IC 130 that can store information generated by the sensors 110 and/or received information (e.g., information received from other WCDs 100 and/or external control circuits). WCD components (e.g., antennas 120, sensors 110, I/O devices 112, ICs 130, communication device 140) can be configured to be removable and/or dynamically positioned using a plurality of predetermined insertion points positioned on one or more surfaces of the WCD 100.

In some embodiments, components of a WCD 100 can be permanently affixed thereto. WCD components can be encapsulated (e.g., to provide a protective barrier) using applicable techniques, including but not limited to injection molding, low pressure injection molding, potting, and lamination. ICS 130 can process data generated by the sensors 110 to facilitate data simplification (e.g., prepare the data in one or more forms that supports credible analysis) and data transmission over cellular networks. ICS 130 can modulate the data transmissions of communication device 140.

In some embodiments, a wearable computing devices ("WCD") for monitoring occupational hazards are disclosed. The WCD may include an apparel item having one or more control circuits affixed thereto. One or more sensors may be communicatively coupled to the computing device and configured to detect or monitor at least one of an aspect of a user of the WCD and an ambient environment of the user. The control circuits can be configured to generate one or more notifications when sensor data comprises a value above a threshold amount. By one approach, one or more I/O devices can be communicatively coupled to the control circuits, where the control circuits can be configured to emit one or more signals via the I/O devices when at least one of the notifications is generated.

In some embodiments, one or more of the sensors can be a microphone. In some embodiments, one or more of the sensors can be an accelerometer. In some embodiments, one or more of the sensors can be configured to detect one or more chemicals. In some embodiments, one or more communications modules may be communicatively coupled to at least one of the control circuits. In some embodiments, the wearable computing device can comprise one or more antennas in electrical communication with one or more of the control circuits. In some embodiments, one or more of the sensors can comprise a graphene-based composition. In some embodiments, one or more of the sensors can be configured to capture one or more temperature values associated with at least one of the user of the WCD and the ambient environment of the WCD. In some embodiments, one or more of the sensors can be configured to capture one or more heartrate values of the user. In some embodiments, one or more of the sensors can be configured to generate geolocational data.

As various modifications could be made in the constructions and methods herein described and illustrated without departing from the scope of the invention, it is intended that all matter contained in the foregoing description or shown in the accompanying drawings shall be interpreted as illustrative rather than limiting. Thus the breadth and scope of the present invention should not be limited by any of the above-described exemplary embodiments, but should be defined only in accordance with the following claims appended hereto and their equivalents.

What is claimed is:

1. A wearable computing device for monitoring occupational hazards comprising:
   an apparel item;
   a control circuit affixed to the apparel item;
   a communications device communicatively coupled to the control circuit;
   an antenna communicatively coupled to the communications device and comprising a component, the component comprising a first conductive composition, the first conductive composition comprising individual sheets of graphene forming a three-dimensional percolated network within the conductive composition;

a sensor communicatively coupled to the control circuit and configured to detect or monitor at least one of an aspect of a user of the wearable computing device and an ambient environment of the user; and wherein the antenna is one or more of removable from and/or dynamically positioned on the apparel item;

the communications device is configured for two-way communication;

the data comprises at least one of voice data, text data, and graphical data;

the sensor comprises a second conductive composition;

the second conductive composition comprises individual sheets of graphene;

the individual sheets of graphene forming a three-dimensional percolated network within the second conductive composition; and the control circuit is configured to generate a notification when sensor data comprises a value above a threshold amount.

2. The wearable computing device of claim 1, further comprising an input/output device communicatively coupled to the control circuit; and wherein in generating the notification the control circuit is further configured to emit a signal via the I/O device when the notification is generated.

3. The wearable computing device of claim 1, wherein the sensor is configured to detect a chemical.

4. The wearable computing device of claim 3, wherein the chemical comprises one or more of propane, methane, carbon monoxide, and a petrochemical.

5. The wearable computing device of claim 1, wherein the control circuit is further configured to modulate a data transmission of the communications device.

6. The wearable computing device of claim 1, wherein the sensor comprises an accelerometer.

7. The wearable computing device of claim 1, wherein the communications device is configured to one or more of transmits and receives data, and wherein the data comprises one or more of voice data, text data, and graphical data.

8. The wearable computing device of claim 1, wherein the sensor is configured to capture a heartrate value of the user.

9. The wearable computing device of claim 1, wherein the sensor is configured to capture geolocation data of the wearable computing device.

10. The wearable computing device of claim 9, wherein the geolocation data comprises one or more of GPS data, time difference of arrival data, Wi-Fi positioning data, and latitude/longitude data.

11. The wearable computing device of claim 1, wherein the apparel item is a vest.

12. The wearable computing device of claim 1, wherein the apparel item is a form fitting apparel item.

13. The wearable computing device of claim 1, wherein the apparel item is an undergarment configured to be worn on a torso or a lower extremity.

14. The wearable computing device of claim 1, wherein the apparel item is an outerwear apparel item.

15. The wearable computing device of claim 1, wherein the conductive composition is applied on to a surface of the apparel item.

* * * * *